(12) United States Patent
Andreu

(10) Patent No.: US 8,950,576 B2
(45) Date of Patent: Feb. 10, 2015

(54) BAG MADE FROM MEDICAL-GRADE PAPER THAT IS TREATED FOR STERILIZATION, WITH STERILIZATION-PROCESS INDICATORS AND PIGMENTED-ADHESIVE-BASED SAFETY FEATURES, WHICH IS EASY TO HANDLE AND USE

(71) Applicant: Albert Pla Andreu, Tlalnepantla (MX)

(72) Inventor: Albert Pla Andreu, Tlalnepantla (MX)

( * ) Notice: Subject to any disclaimer, the term of this patent is extended or adjusted under 35 U.S.C. 154(b) by 69 days.

(21) Appl. No.: 13/902,730

(22) Filed: May 24, 2013

(65) Prior Publication Data

US 2014/0154131 A1 Jun. 5, 2014

Related U.S. Application Data

(63) Continuation of application No. 13/499,611, filed as application No. PCT/MX2010/000098 on Sep. 29, 2010, now abandoned.

(30) Foreign Application Priority Data

Sep. 30, 2009 (MX) .................... MX/a/2009/010520

(51) Int. Cl.
*A61L 2/00* (2006.01)
*B32B 15/04* (2006.01)
(Continued)

(52) U.S. Cl.
CPC .............. *A61L 2/28* (2013.01); *A61B 19/0264* (2013.01); *A61B 2019/0267* (2013.01); *A61L 2202/181* (2013.01)
USPC ......... 206/63.5; 206/63.3; 206/438; 206/439; 206/363; 53/425; 53/52; 53/285; 383/207; 229/80; 229/53; 229/62; 428/34.2; 428/343; 422/294

(58) Field of Classification Search
CPC ............. B65D 1/28; B65D 3/264; A61J 1/00; A61L 2/00; B31B 2219/00
USPC .................... 53/425, 52, 285; 206/63.5, 63.3, 206/438–439, 363; 383/207; 229/80, 53, 229/62; 428/34.2, 343; 422/26, 28, 119, 422/294, 50
See application file for complete search history.

(56) References Cited

U.S. PATENT DOCUMENTS

| | | | |
|---|---|---|---|
| 3,245,607 A | * | 4/1966 | Kelson .......................... 116/207 |
| 4,194,622 A | | 3/1980 | Lewis |

(Continued)

FOREIGN PATENT DOCUMENTS

| | | |
|---|---|---|
| GB | 1459295 | 12/1976 |
| MX | 9806678 | 2/2000 |
| WO | WO 00/71433 | 11/2000 |

OTHER PUBLICATIONS

U.S. Appl. No. 13/499,611, filed May 22, 2012; Albert Pla Andreu; Office Action dated Feb. 28, 2013.

(Continued)

*Primary Examiner* — Monzer R Chorbaji
(74) *Attorney, Agent, or Firm* — Thorpe North & Western LLP

(57) ABSTRACT

The present invention relates to bags made from medical-grade paper for sterilization, with sterilization-process indicators and pigmented-adhesive-based safety features, which is easy to handle and use and can be used to store materials, more particularly surgical medical material, for sterilization. Such bags are produced using medical-grade paper that is treated on the surface thereof with a microbiocide for sterilization, and, owing to the structure and design thereof, allow safe, rapid handling of the sterilized material placed within, since there are visual indicators that guarantee the hermetic closure and sealing thereof. Furthermore, generally, the invention has printed indicators that change color depending on the sterilization process carried out on the bags and on whether said process was carried out correctly.

10 Claims, 4 Drawing Sheets

(51) Int. Cl.
    *B65D 33/00*     (2006.01)
    *A61B 19/02*     (2006.01)
    *B65D 83/10*     (2006.01)
    *B65B 19/28*     (2006.01)
    *A61L 2/28*     (2006.01)

(56) References Cited

U.S. PATENT DOCUMENTS

| | | |
|---|---|---|
| 4,818,120 A | 4/1989 | Addiego |
| 5,655,653 A | 8/1997 | Chester |
| 5,797,243 A | 8/1998 | Tagliaferri et al. |
| 2005/0194060 A1 | 9/2005 | Houwaert et al. |
| 2009/0252905 A1 | 10/2009 | Hill et al. |

OTHER PUBLICATIONS

PCT/MX2010/000098; filed Sep. 29, 2010; Albert Pla Andreu; International Search Report dated Jul. 5, 2011.

* cited by examiner

BAG MADE FROM MEDICAL-GRADE PAPER THAT IS TREATED FOR STERILIZATION, WITH STERILIZATION-PROCESS INDICATORS AND PIGMENTED-ADHESIVE-BASED SAFETY FEATURES, WHICH IS EASY TO HANDLE AND USE

FIELD OF THE INVENTION

The present invention relates to bags made from medical-grade paper for sterilization with sterilization-process indicators and pigmented-adhesive based safety features, which are easy to handle and use and can be used to store materials, more particularly surgical medical materials.

BACKGROUND OF THE INVENTION

Previously used surgical medical materials need to be sterilized prior to subsequent use. These different types of instruments and mechanical pieces are placed within a sterilization bag that has a region that is permeable to gas but impermeable to germs and bacteria. After sealing the bag, the sterilization is realized with a method using high temperature steam, ethylene oxide gas (EOG), and similar.

After the sterilization of the instruments, but before their use in surgery, the instruments are stored within the bag. During the surgery or the treatment, the bag is opened and the instruments are used.

At present, the designs of existing bags in the market present some disadvantages. For example, access to the sterilized material inside the bag can be inefficient and slow because the bag lacks devices and fittings necessary for such access. Another disadvantage of the existing designs is that some materials, such as tweezers and bistouries, have a weight and design that can break the bags due to an insufficiently resistant bottom. In addition, another disadvantage is the fact that they lack visual indicators that allow visualization of whether the bag is perfectly sealed, that can distinguish the type of sterilization used, and that can distinguish whether the sterilization was carried out in a correct manner, so as to guarantee the security of the bag's seal as well as the sterilization process.

The patent application EP 1550466A relates to a sterilization bag, used to store and to sterilize medical instruments that have sharp edges. The lateral edges and bottom are made of a gas- and steam-permeable material and of a material that is adhered to an upper opening, but this is different from the bag of the present invention.

The Mexican patent No. 178951 teaches a bag for sterilization of material, which incorporates a device for fast and safe opening of the bags once the material is sterilized, but that is also different from the bag of the present invention.

The Mexican patent application 1998/00678 teaches a bag for sterilization and conservation of material, which is similar to the bag of the present invention. It is made of a piece of flexible material like paper, which has a rectangular configuration. It is closed at its lower end with a double or triple bottom, two lateral sides which have a folded or bellows shape. The upper part, which constitutes the mouth or entrance of the bag for introducing the material to be sterilized, has a saw-toothed pattern along its width. The bag relies on a thread that is hidden in the internal part of the side folds to open the bag with greater rapidity and facility, but this bag is different from the bag of the present invention. The bag of the present invention has a double bottom along its lower edge, but this double bottom has an inner thermo-weldable pigmented-adhesive to achieve its hermetically sealed closure. The pigmentation of the adhesive allows visualization of whether it is perfectly sealed or not, guaranteeing its total hermetic closure. In the upper front there is a notch (for easy opening with a finger) in the central part facilitating the opening of the bag. The front and back of the upper part also have a sawed edge to prevent the personnel who use the bags from cutting themselves. In addition, the part where the thread comes off has a straight edge rather than a sawed edge, which facilitates, in a surprising way, the obtaining of the segment of paper for subsequent opening of the sterilized bag, hence avoiding the difficulty of opening the bag. In addition, the bag uses an inner thermo-weldable pigmented-adhesive for closing the upper part, which pigmentation allows visualization of whether the bag is perfectly sealed or not, thus guaranteeing its hermetic closure and sealing. The bag is closed longitudinally with a double line of pigmented adhesive, which guarantees a double security seal. This pigmentation allows visualization of whether or not the bag is perfectly sealed. In addition it has two indicators of sterilization that change color depending on the sterilization process carried out on the bags. It contains a legend and instructions of use in a water-based ink. This water-based ink can be used to identify whether there is a leak of water or steam in the sterilization process if the ink has flowed. For these reasons, this invention solves problems and has advantages that are not solved with the bag of the patent application 1998/006678 and the bag of the present invention is new and inventive in light of the present document.

The Mexican patent application 1999/001855 protects a procedure of applying a chemical agent with germicidal characteristics to the medical grade paper for the manufacture of bags of paper, mixed bags, etc. This will prevent these packages from serving as a vector or transport of microorganisms present in the environment or by manipulation.

This procedure comprises the following steps: a) The impregnation on the surface of the medical grade paper, with paper weight between 30 up to 100 g/m$^2$, with an alcoholic solution of triclosan from 0.2% to 3.8% or an aqueous solution of benzalconium chloride from 0.2% to 3.8%, which must remain after the sterilization process is carried out; b) The impregnation of step a) is performed by flexographic impression or by means of photogravure or by coating and c) drying at a temperature of from 30° C. to 190° C. for an aqueous solution of benzalconium chloride and from 30° C. to 70° C. for an alcoholic solution of triclosan.

The bag of the present invention has new characteristics of design and manufacture that contribute to solving the problems of presently used bags for sterilization of material, which is why it is new and inventive in the light of the previous documents.

BRIEF DESCRIPTION OF THE INVENTION

The present invention relates to bags for sterilization procedures made from medical grade paper having sterilization-process indicators and pigmented-adhesive based safety features, which are easy to handle and use. Access to the sterilized material used in treatments or surgical procedures must be fast and safe. One objective of the present invention is the manufacture of a paper bag for sterilization procedures made from medical grade paper that is treated on the surface with a microbiocide and has new characteristics of design for sealing, handling, and easy opening, in addition to indicators of sealing and sterilization of the bag.

One embodiment of the present invention is to provide a bag made from medical-grade paper, the paper being treated with a microbiocide that allows for sterilization of instruments used in surgical treatments.

In accordance with another embodiment of the present invention, a paper bag used in the sterilization of surgical articles allows express and easy access to the sterilized material placed inside of the bag.

Another embodiment of the present invention is to provide a bag for sterilization of surgical instruments with a sufficiently resistant bottom to hold surgical instruments that by their design and weight induce the breaking of the bag.

The invention is also directed to the manufacture of a bag that is easy to open subsequent to sterilization with a sawed edge that avoids injury of the personnel who fill the bags, but the end is straight to facilitate opening the bag.

Figure 1:
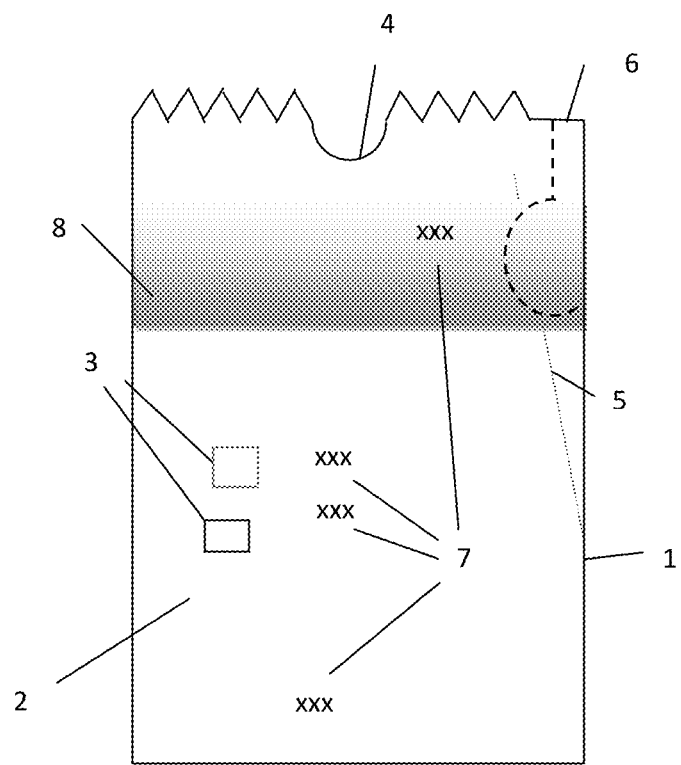
FIG. 1 is a schematic view of an embodiment of the front side of the bag in conformity with the present invention in which, 1 represents a bag made of medical-grade paper, 2 represents the medical-grade paper treated on the surface thereof with a germicide for sterilization (SUPERANTI®) 3 represents printed indicators that change color depending on the sterilization process to which they are subjected, 4 represents the notch for easy opening of the bag, 5 represents a threaded system for easy opening after sterilization, 6 represents the part where the edge is straight rather than saw-shaped and where the thread is detached for easily obtaining that paper segment, indicating to pull and tear along the dotted line to open the bag, 7 represents a legend and instructions in a water-based ink and 8 is the thermo-weldable adhesive in the upper part of the bag.
Figure 2:
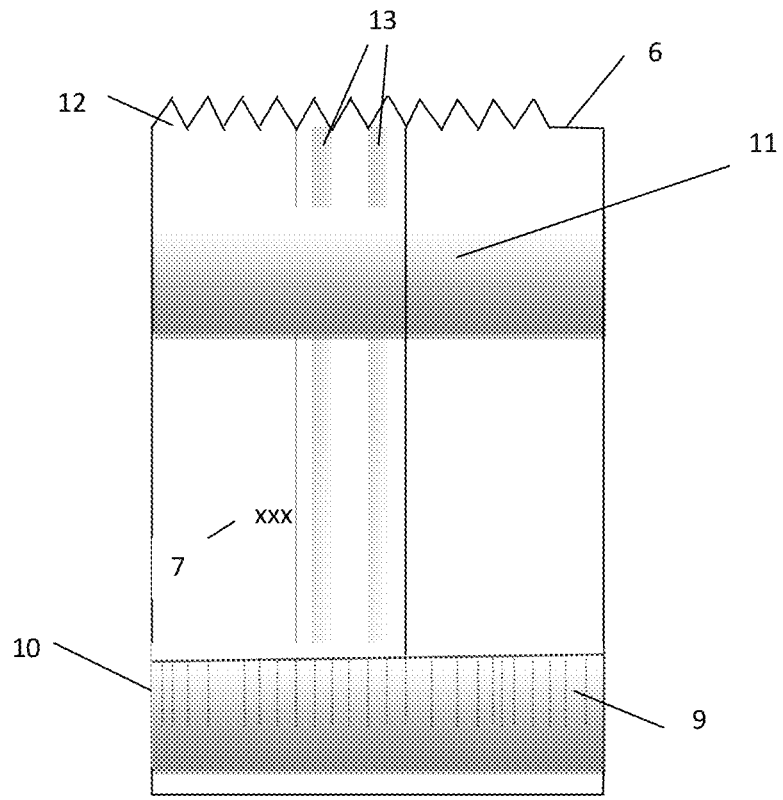
FIG. 2 is a schematic view of an embodiment of the reverse side of the bag in conformity with the present invention in which, 9 represents a double fold at the bottom of the bag, represents a pigmented interior thermo-weldable adhesive hermetically sealing the bottom of the bag, 11 represents an pigmented adhesive for closing the upper part, 12 represents a sawed edge to prevent the personnel filling the bag from injuring themselves, 6 represents the part where the edge is straight rather than saw-shaped and where the thread is detached for easily obtaining that paper segment, 7 represents a legend and instructions in a water-based ink, 13 represents a double line of inner pigmented adhesive for closing the bag longitudinally for double security with visual confirmation of continuity.
Figure 3A:
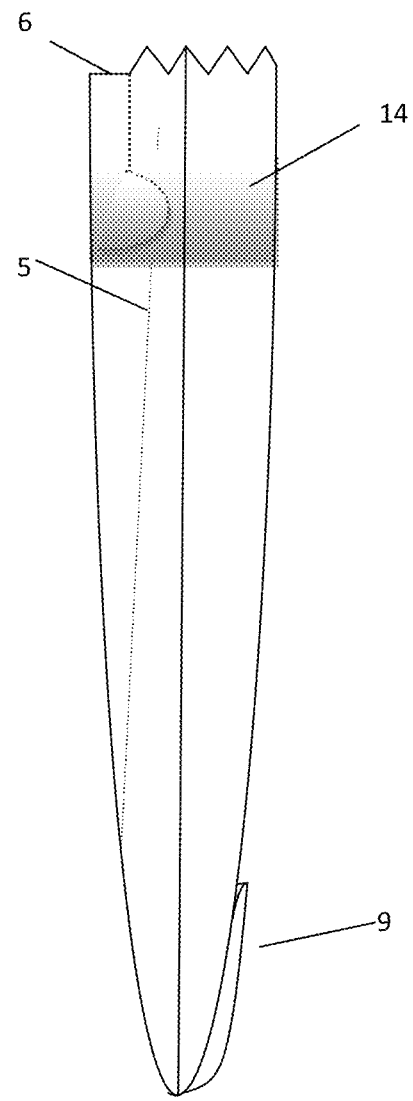
FIG. 3a is a schematic view of an embodiment of the right side of the bag in accordance to the present invention in which, 5 represents a threaded system for easily opening the bag after sterilization, 6 represents the part where the edge is straight rather than saw-shaped and where the thread is detached for easily obtaining that paper segment, 9 represents a double fold on the bottom of the bag, and 14 represents a lateral side which has a folded or bellows shape.
Figure 3B:
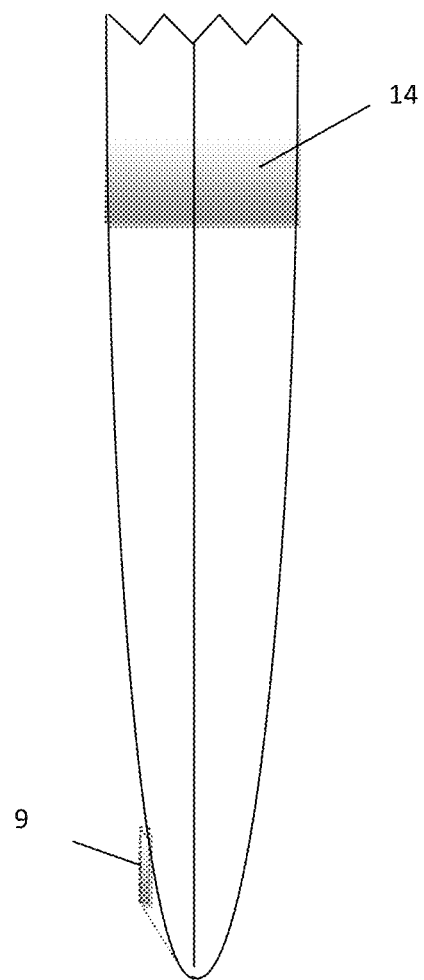

The FIG. 3b is a schematic view of an embodiment of a left lateral side of the bag in accordance with the present invention in which, 9 represents a double fold on the bottom of the bag, 14 represents a lateral side which has a folded or bellows shape.

DESCRIPTION OF THE INVENTION

The bag of the present invention is a bag made from medical-grade paper treated on the surface with a microbiocide for sterilization. Due to the structure and design thereof, the bag allows safe and rapid handling of the sterilized material placed within because of the visual indicators that guarantee the hermetic closure and sealing thereof. Furthermore, generally the invention has printed indicators that change color depending on the sterilization process carried out on the bags and on whether said process was carried out correctly.

The bag of the present invention is capable of solving the problems of sealing, easy opening, and easy handling, in addition to the sterilization indicators and the legends and instructions in water-based ink which provide a guarantee that the sterilization process was carried out correctly.

The bag of the present invention is made from a piece of flexible material such as medical-grade paper treated on the surface for sterilization with germicidal agent (SUPERANTI®). The bag has a rectangular or square configuration, closed at its lower edge with a double bottom. This double bottom relies on a pigmented inner thermo-weldable adhesive to hermetically seal the bottom. The pigmentation of the adhesive provides visualization of whether or not the bag is perfectly sealed, guaranteeing a hermetic closure. The bag has two lateral sides that have a folded or bellows shape. The upper part of the bag can be used to introduce the material to be sterilized. In addition, the upper front part has a notch in the center for easily opening the bag. The upper front and back sides have a sawed edge to prevent the personnel using the bag from cutting themselves, but the part where the thread is located is straight rather than saw-shaped. This facilitates, in a surprising way, obtaining the segment of paper for opening the bag after sterilization, thus avoiding the difficulty of its opening. In addition, an inner pigmented thermo-weldable adhesive is used for closing the upper part. The pigmentation of the adhesive provides visualization of whether or not the closure is perfectly sealed, guaranteeing its total hermetic closure. A thread is hidden within the profile of the fold so as to open the bag with greater rapidity and facility. The bag is closed longitudinally with a double line of pigmented adhesive, which guarantees double security of seal. The pigmentation of the adhesive provides visualization of whether or not the closure is perfectly sealed. Additionally, the bag has two indicators that change color depending on the sterilization process to which the bags are subjected. The bag also contains a legend and instructions for use in water-based ink, which can identify if condensate or steam was used in the sterilization process if the ink has flowed.

The dimensions of the bags vary from 5 to 90 cm in length and from 5 to 90 cm in width. The bag has printed indicators of sterilization that change color according to the process to which they are subjected. For example, if the bag is sterilized in steam, the color of the indicator changes to blue-gray. Alternatively, if the bag is sterilized in ethylene oxide gas (E.O.), the indicator changes light brown-blue.

Because the method used for sterilization is generally performed using high temperature humidity and ethylene oxide gas, it is necessary that the material used to make the bag will be an effective material for sterilization. This is why the bag is made of medical-grade paper treated on the surface for sterilization with a germicidal agent (SUPERANTI®).

The paper bag characteristic of the present invention includes a pigmented thermo-weldable adhesive in its interior to hermetically seal the bottom and an interior pigmented thermo-weldable adhesive for closing the top.

The bag is closed longitudinally with one double line of pigmented adhesive to have double security with visual confirmation of continuity.

The methods of manufacture of the bags of the present invention are known by those skilled in the art, and should not be difficult to perform.

The adhesives, the process indicators, and the medical grade paper are also known by those skilled in the art.

The invention claimed is:

1. A bag made from medical-grade paper for sterilization having sterilization-process and safety indicators, comprising:
   a lower edge with a double bottom, the double bottom having an inner pigmented thermo-weldable adhesive adapted to hermetically seal the lower edge;
   two lateral sides having a folded or bellows shape;
   an upper part, which constitutes the mouth or entrance of the bag for introducing materials to be sterilized, including a notch in an upper front part in the center for easy opening of the bag, the upper front and an upper back having a sawed edge, but a part where a thread is located being straight rather than saw-shaped, wherein the straight part facilitates obtaining a segment of paper for opening the bag after sterilization, and wherein the upper part has an inner pigmented thermo-weldable adhesive for closing the upper part;
   a profile of a fold having the thread hidden in an internal part of the profile, adapted to open the bag with greater rapidity and facility;
   a double pigmented adhesive line, wherein the bag is closed longitudinally via the double pigmented adhesive line and where the double pigmented adhesive line guarantees a double security of sealing;
   two indicators of sterilization that change color according to the sterilization process to which the bag is subjected; and
   a legend and instructions of use in water-based ink.

2. A bag made from medical-grade paper for sterilization according to claim 1, wherein the sawed edge prevents personnel filling the bag from getting cut, but where the part where the thread is located is straight rather than saw-shaped, wherein the straight part facilitates obtaining a segment of paper used for opening after sterilization.

3. A bag made from medical-grade paper for sterilization according to claim 1, wherein the inner pigmented thermo-weldable adhesive forms a hermetic seal at the bottom includes a pigmentation of the adhesive providing visualization of whether or not the bottom is perfectly sealed, guaranteeing its total hermetic closure.

4. A bag made from medical-grade paper for sterilization according to claim 1, wherein the inner pigmented thermo-weldable adhesive for closing the upper part, includes a pigmentation that provides visualization of whether or not the upper part is perfectly sealed, guaranteeing its total hermetic closure.

5. A bag made from medical-grade paper for sterilization according to claim 1, wherein the double line of pigmented adhesive, which guarantees a double security of sealing, includes a pigmentation that provides visualization of whether or not the double line is perfectly sealed, guaranteeing its total hermetic closure.

6. A bag made from medical-grade paper for sterilization according to claim 1, further comprising a system with a thread adapted to easily open the bag subsequent to sterilization.

7. A bag made from medical-grade paper for sterilization according to claim 1, wherein the part where the thread is located is straight, allowing the segment of paper to be easily obtained for opening the bag.

8. A bag made from medical-grade paper for sterilization according to claim 1, having indicators that change color according to the sterilization process to which it is subjected.

9. A bag made from medical-grade paper for sterilization according to claim 1, wherein the legend and instructions of use in water-based ink are indicators to identify whether there is condensate steam in the sterilization process based on whether the ink flowed.

10. A bag made from medical-grade paper for sterilization according to claim 1, wherein the dimensions of the bag are from 5 to 90 cm in length and from 5 to 90 cm in width.

\* \* \* \* \*